United States Patent
Kondo

(10) Patent No.: US 9,282,936 B2
(45) Date of Patent: Mar. 15, 2016

(54) IMAGE DIAGNOSTIC APPARATUS, X RAY COMPUTED TOMOGRAPHY APPARATUS, MEDICAL BED APPARATUS, AND BED CONTROL METHOD

(71) Applicants: Kabushiki Kaisha Toshiba, Minato-ku (JP); Toshiba Medical Systems Corporation, Otawara (JP)

(72) Inventor: Gen Kondo, Otawara (JP)

(73) Assignees: KABUSHIKI KAISHA TOSHIBA, Minato-ku (JP); Toshiba Medical Systems Corporation, Otawara-shi (JP)

(*) Notice: Subject to any disclaimer, the term of this patent is extended or adjusted under 35 U.S.C. 154(b) by 133 days.

(21) Appl. No.: 14/099,377

(22) Filed: Dec. 6, 2013

(65) Prior Publication Data

US 2014/0098934 A1 Apr. 10, 2014

Related U.S. Application Data

(63) Continuation of application No. PCT/JP2013/064070, filed on May 21, 2013.

(30) Foreign Application Priority Data

Jun. 12, 2012 (JP) ................................ 2012-133272

(51) Int. Cl.
  *A61B 6/04* (2006.01)
  *A61B 6/03* (2006.01)
  *A61B 5/055* (2006.01)

(52) U.S. Cl.
  CPC ............... *A61B 6/0407* (2013.01); *A61B 6/032* (2013.01); *A61B 6/0457* (2013.01); *A61B 5/0555* (2013.01)

(58) Field of Classification Search
  CPC ...... A61B 6/04; A61B 6/0457; A61B 6/0442; A61B 5/0555; A61B 6/0407
  See application file for complete search history.

(56) References Cited

U.S. PATENT DOCUMENTS 5,825,843 A * 10/1998 Kobayashi ...................... 378/20
2005/0234327 A1 * 10/2005 Saracen et al. ................ 600/407

FOREIGN PATENT DOCUMENTS

| CN | 101217913 A | 7/2008 |
| JP | 11-253437 A | 9/1999 |
| JP | 2599544 Y2 | 9/1999 |
| JP | 2009-291281 A | 12/2009 |

OTHER PUBLICATIONS

International Search Report mailed Jul. 9, 2013 for PCT/JP2013/064070 filed on May 21, 2013 with English Translation of Categories.

(Continued)

*Primary Examiner* — Hoon Song
(74) *Attorney, Agent, or Firm* — Oblon, McClelland, Maier & Neustadt, L.L.P.

(57) ABSTRACT

According to one embodiment, a support mechanism movably supports the table top. A bed driver generates driving power to be supplied to the support mechanism to move the table top. An imaging mechanism includes a mechanism for acquiring medical image data associated with a subject placed on the table top. An ascending switch receives an ascending instruction for the table top. A descending switch receives a descending instruction for the table top. A storage unit stores the height of the table top at the time of the issuance of an ascending instruction as a target return position. When a descending instruction is issued, a bed controller controls the bed driver to descend the table top to the target return position stored in the storage unit.

8 Claims, 9 Drawing Sheets

(56) References Cited

OTHER PUBLICATIONS

International Written Opinion mailed Jul. 9, 2013 for PCT/JP2013/064070 filed on May 21, 2013.

International Search Report issued on Jul. 9, 2013, in Patent Application No. PCT/JP2013/064070 filed on May 21, 2013 (submitting English translation only).

Office Action mailed Dec. 7, 2015 in Chinese Patent Application No. 201380000574.2.

* cited by examiner

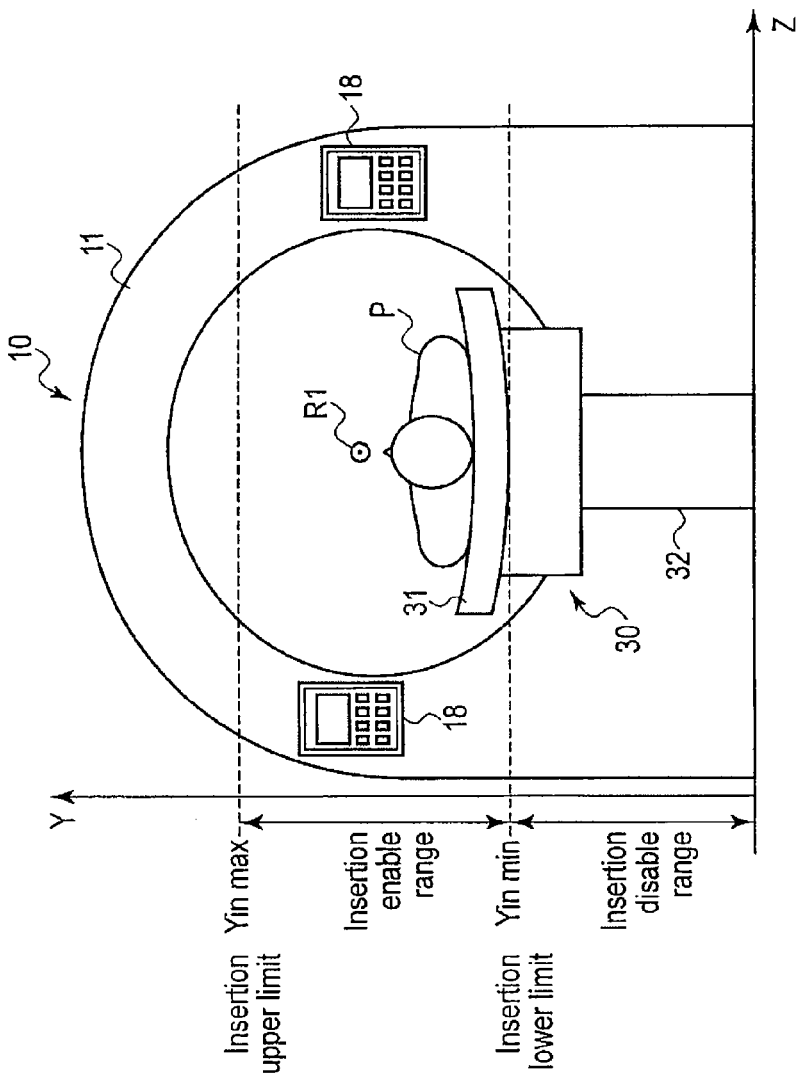
F I G. 4

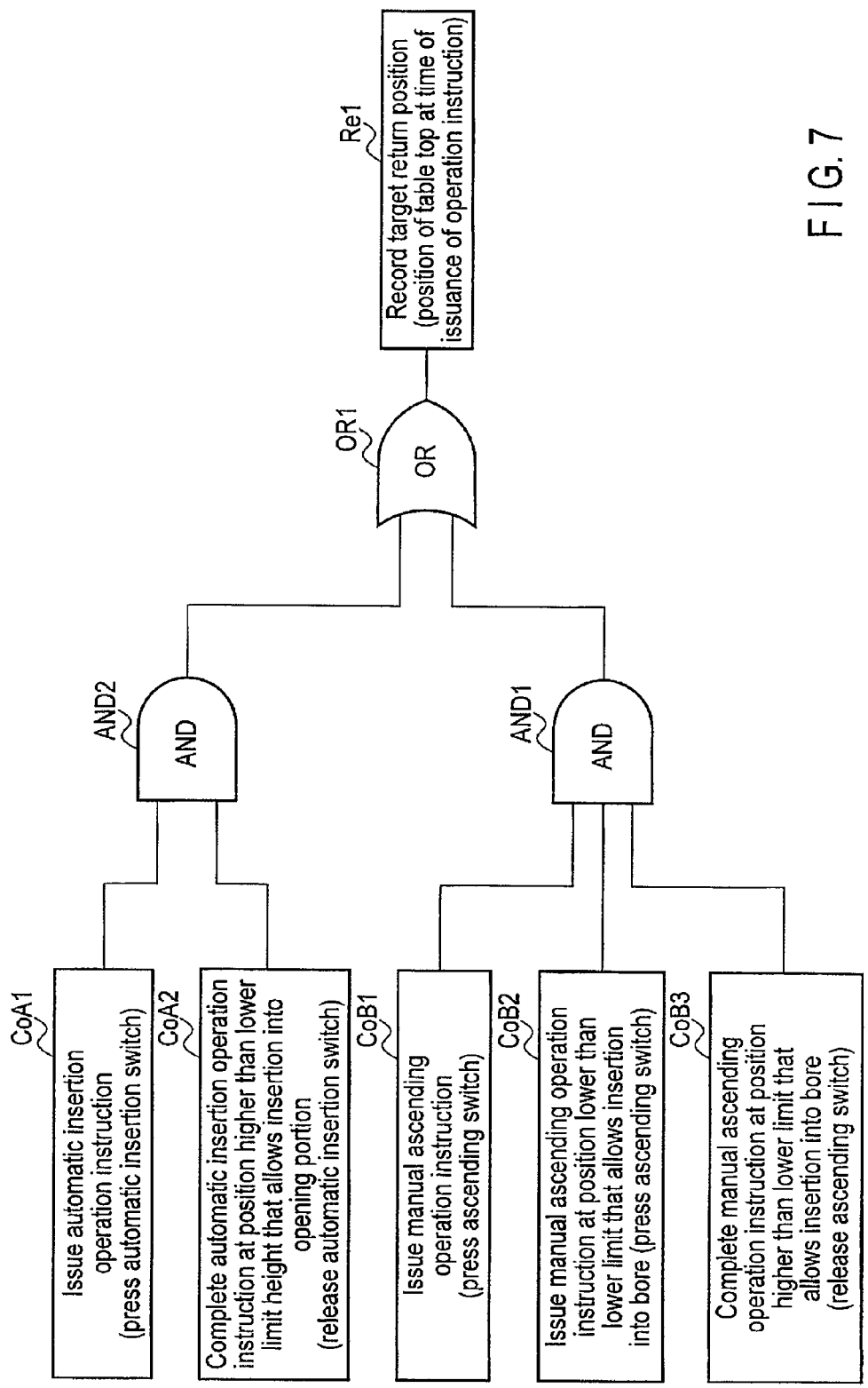
F I G. 7

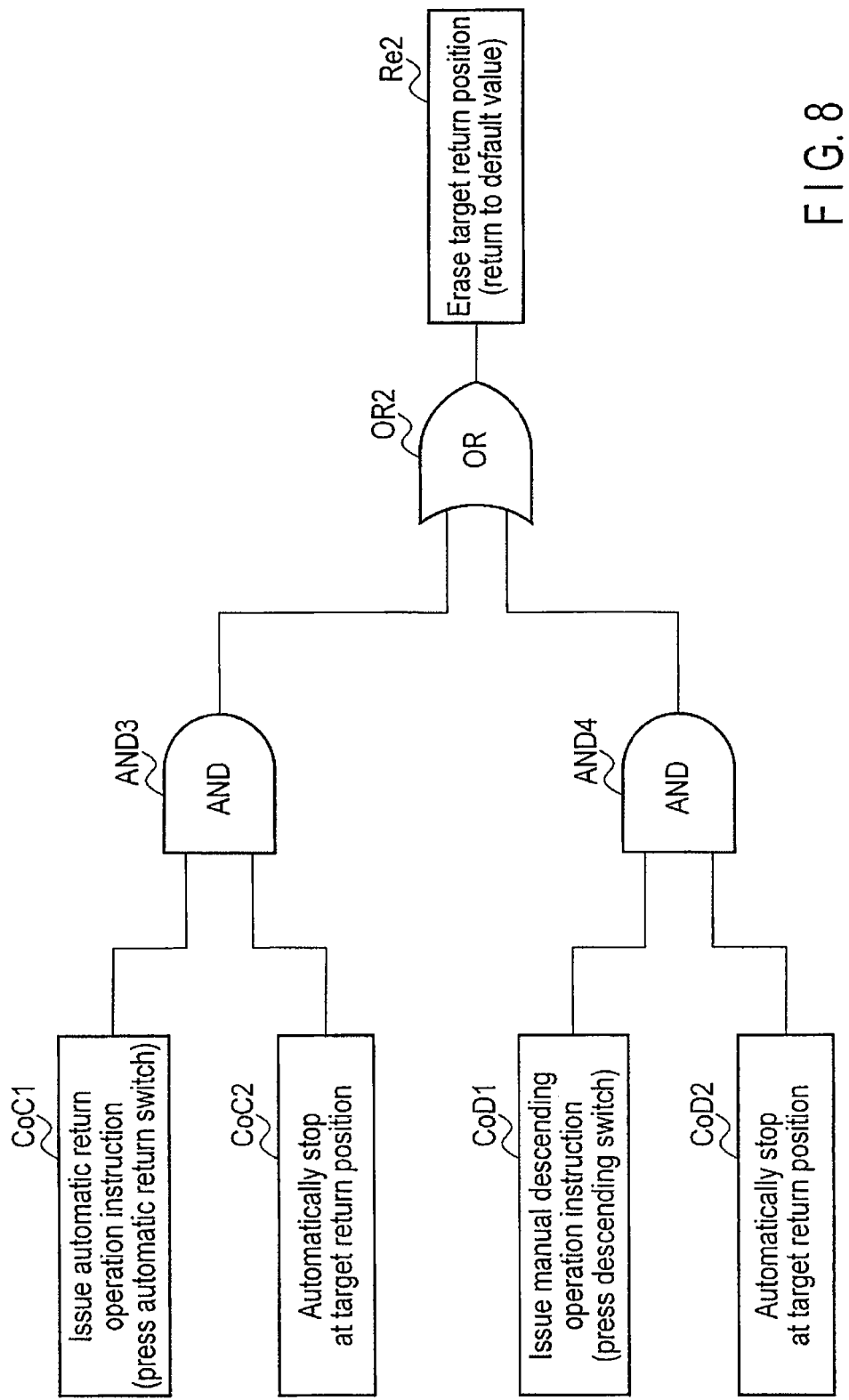
F I G. 8

IMAGE DIAGNOSTIC APPARATUS, X RAY COMPUTED TOMOGRAPHY APPARATUS, MEDICAL BED APPARATUS, AND BED CONTROL METHOD

CROSS-REFERENCE TO RELATED APPLICATIONS

This application is a Continuation application of PCT Application No. PCT/JP2013/064070, filed May 21, 2013 and based upon and claims the benefit of priority from the Japanese Patent Application No. 2012-133272, filed Jun. 12, 2012, the entire contents of all of which are incorporated herein by reference.

FIELD

Embodiments described herein relate generally to an image diagnostic apparatus, X-ray computed tomography apparatus, medical bed apparatus, and bed control method.

BACKGROUND

An X-ray computed tomography apparatus has an automatic insertion function and automatic return function for the table top. The automatic insertion function is a function of moving the table top to a predetermined automatic stop position inside the bore of a gantry to place an imaging region of a patient placed on the table top in an FOV inside the bore. The automatic return function is a function of returning the table top from inside the bore to a predetermined automatic stop position outside the bore to allow the patient to get out of the table top after CT imaging.

Patients differ in shape, height, age, condition, and the like, and hence the table top height that allows the patient to get out of the table top differs for the respective patients. The height of an automatic stop position in the automatic return function is set to the value decided in advance by the operator or maker. Providing a plurality of automatic return switches can assign different heights to the respective automatic return switches. It is however impossible to set the height of an automatic stop position to an optimal height for each patient. For this reason, the operator needs to manually move the table top from the automatic stop position to a height allowing each patient to easily get out of the table top after the table top is returned to the automatic stop position by using the automatic return function.

BRIEF DESCRIPTION OF THE DRAWING

FIG. 4 is a side view of the gantry and medical bed apparatus in FIG. 1 when viewed from the Z-axis direction.

FIG. 7 is a view showing another target return position setting algorithm executed by the storage controller in step S4 in FIG. 5.

FIG. 8 is a view showing a target return position erase algorithm executed by the storage unit in step S7 in FIG. 5.

DETAILED DESCRIPTION

An image diagnostic apparatus, X-ray computed tomography apparatus, medical bed apparatus, and bed control method according to an embodiment will be described below with reference to the accompanying drawings.

In general, according to one embodiment, an image diagnostic apparatus includes a table top, a support mechanism, a driving power generator, an imaging mechanism, a first operation unit, a second operation unit, a storage unit, a movement controller. The table top is for a subject. The support mechanism is movably support the table top. The driving power generator generates driving power to be supplied to the support mechanism to move the table top. The imaging mechanism is configured to acquire medical image data associated with the subject placed on the table top. The first operation unit is configured to receive an ascending instruction for the table top. The second operation unit is configured to receive a descending instruction for the table top. The storage unit stores a reference height of the table top at the time of issuance of the ascending instruction. The movement controller controls the driving power generator to descend the table top to the reference height upon issuance of the descending instruction.

The image diagnostic apparatus according to this embodiment can be applied to any type of apparatus which uses a medical bed apparatus and an imaging mechanism for acquiring medical image data associated with a subject (patient) placed on the medical bed apparatus. For example, as an image diagnostic apparatus according to this embodiment, an X-ray computed tomography apparatus, magnetic resonance imaging apparatus, SPECT apparatus, PET apparatus, radiation therapy apparatus, or the like can be applied. For the sake of a concrete description, assume that in the following description, the image diagnostic apparatus according to the embodiment is an X-ray computed tomography apparatus.

Figure 1:
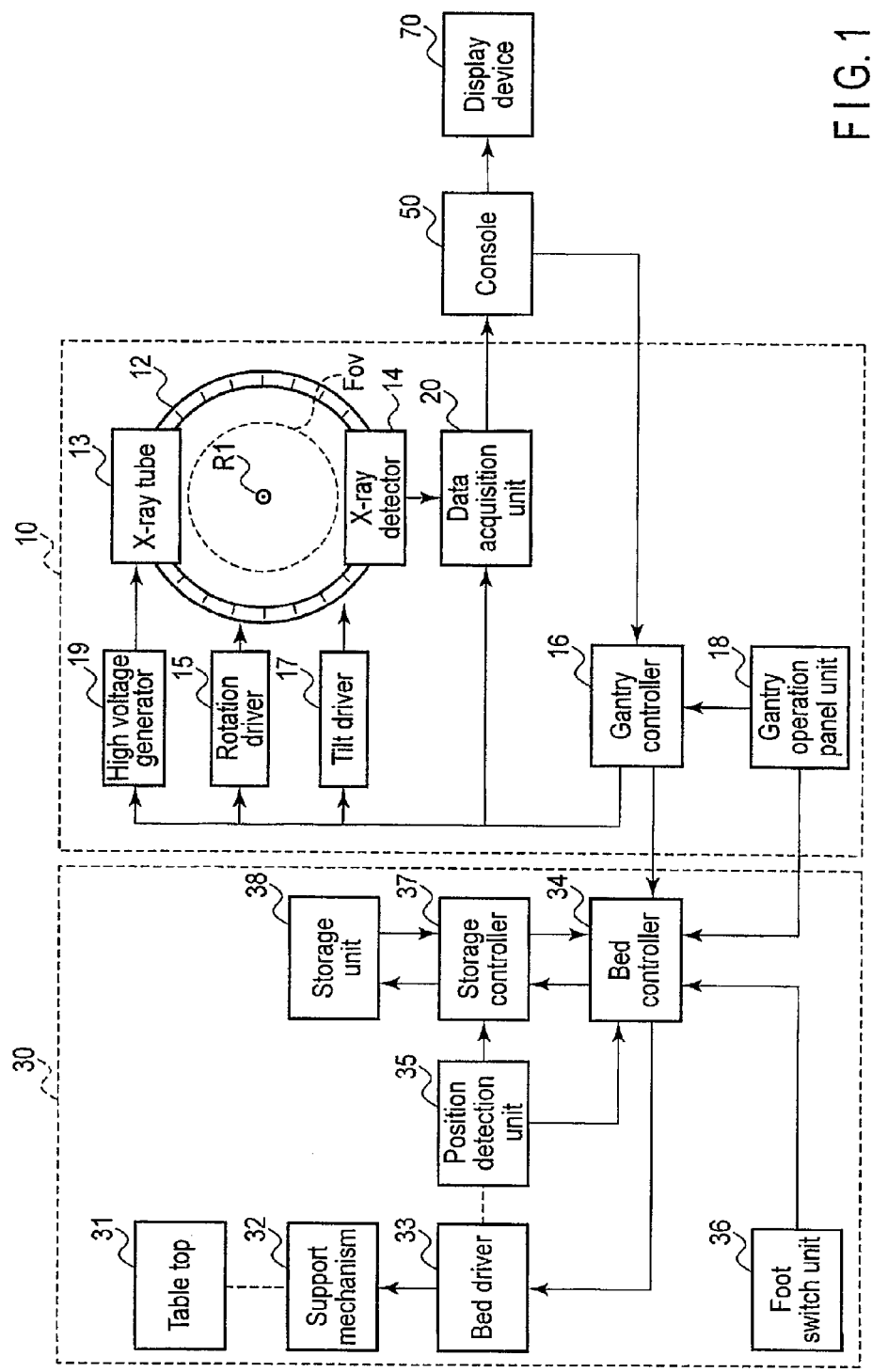
FIG. 1 is a block diagram showing the arrangement of an X-ray computed tomography apparatus according to an embodiment.
Figure 2:
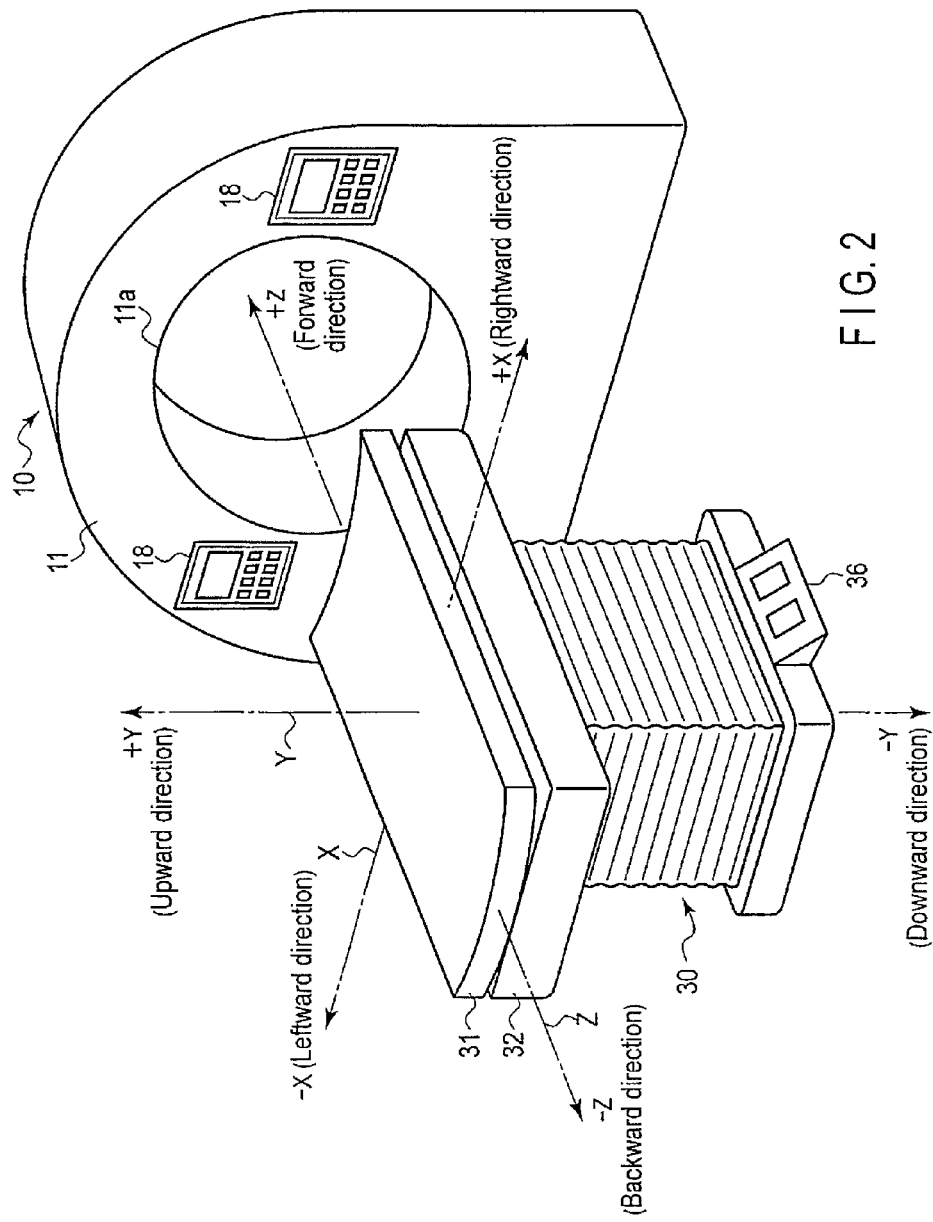
FIG. 2 is a perspective view of a gantry and medical bed apparatus in FIG. 1.

FIG. 1 is a block diagram showing the arrangement of an X-ray computed tomography apparatus according to this embodiment. FIG. 2 is a perspective view of a gantry 10 and a medical bed apparatus 30. The gantry 10 and the medical bed apparatus 30 are installed in, for example, a CT imaging room. A console 50 is installed in a control room or the like adjacent to the CT imaging room.

As shown in FIG. 2, the gantry 10 has a gantry housing 11 in which a bore 11a having an almost cylindrical shape is formed. A rotating ring 12 having an almost cylindrical shape is mounted in the gantry housing 11. The gantry housing 11 supports the rotating ring 12 so as to allow it to rotate about a rotation axis R1. An X-ray tube 13 and an X-ray detector 14 are mounted on the rotating ring 12 so as to face each other through the rotation axis R1. A partial spatial region of the bore 11a is set for an FOV (Field Of View). A table top 31 is inserted into the bore 11a. The rotating ring 12 rotates around the rotation axis R1 at a predetermined angular velocity upon receiving a driving signal from a rotation driver 15. The rotation driver 15 supplies a driving signal to the rotating ring 12 in accordance with a control signal from a gantry controller 16.

In addition, the gantry housing 11 supports the rotating ring 12 so as to allow it to tilt relative to a vertical axis (not shown). The rotating ring 12 tilts relative to the vertical axis upon receiving a driving signal from a tilt driver 17. The tilt driver 17 supplies a driving signal to the rotating ring 12 in accordance with a control signal from the gantry controller 16.

As shown in FIG. 2, operation panel units 18 having operation panels allowing the operator to perform manual operation are attached the front surface of the gantry housing 11. The operation panel units 18 each include a plurality of switches for operating the gantry 10 and the medical bed apparatus 30. The operation panel units 18 are provided on the two sides of the bore 11a to improve operator friendliness. An instruction signal corresponding to a switch for operation on the gantry 10 is supplied to the gantry controller 16. An instruction corresponding to a switch for operation on the medical bed apparatus 30 is supplied to a bed controller 34.

The X-ray tube 13 generates X-rays upon receiving a high voltage and a filament current from a high voltage generator 19. The high voltage generator 19 applies a high voltage based on a control signal from the gantry controller 16 to the X-ray tube 13, and supplies a filament current based on a control signal from the gantry controller 16 to the X-ray tube 13.

The X-ray detector 14 detects the X-rays generated from the X-ray tube 13. The X-ray detector 14 is provided with a plurality of two-dimensionally arrayed detection elements. Each detection element detects X-rays from the X-ray tube 13, and generates an electrical signal corresponding to the energy of detected X-rays. The generated electrical signal is supplied to a data acquisition unit (DAS: Data Acquisition System) 20. The data acquisition unit 20 acquires electrical signals for each view via the X-ray detector 14 under the control of the gantry controller 16. The data acquisition unit 20 converts acquired analog electrical signals into digital data. Digital data is called raw data. Raw data is supplied to a console 50.

The gantry controller 16 controls the rotation driver 15, the tilt driver 17, the high voltage generator 19, the data acquisition unit 20, and bed controller 34 of the medical bed apparatus 30 in accordance with the imaging conditions and imaging protocols supplied from the console 50 and instruction signals from the gantry operation panel unit 18.

As shown in FIG. 2, the medical bed apparatus 30 is installed near the gantry 10. The medical bed apparatus 30 includes the table top 31 for a subject. A support mechanism 32 supports the table top 31 so as to allow it to move in a three-dimensional space. The support mechanism 32 positions the table top 31 so as to align the body axis of the subject placed on the table top 31 with the rotation axis R1 of the rotating ring 12. Note that the long axis of the table top 31 is defined as the Z-axis, the short axis of the table top 31 is defined as the X-axis, and the vertical axis perpendicular to the Z- and X-axes is defined as the Y-axis. Assume that the front direction (+Z direction) when viewed from the operator standing facing the front surface of the gantry housing 11 is called the forward direction, and the back direction (−Z direction) is called the backward direction. The rightward direction (+X direction) when viewed from the operator standing facing the front surface of the gantry housing 11 is called the rightward direction without any change, and the leftward direction (−Z direction) is called the leftward direction without any change. Assume also that the direction (+Y direction) in which the table top 31 moves upward is called the upward direction, and the direction (−Y direction) in which the table top 31 moves downward is called the downward direction.

The support mechanism 32 supports the table top 31 so as to allow it to freely move along the X-, Y-, and Z-axes. The support mechanism 32 moves the table top 31 upon receiving a driving signal from a bed driver 33. The bed driver 33 supplies a driving signal to the support mechanism 32 in accordance with a control signal from the bed controller 34. The bed driver 33 includes a motor (driving power generator) such as a servo motor built in the medical bed apparatus 30. The motor is provided for each movable axis of the table top 31. The support mechanism 32 may support the table top 31 so as to allow it to move along movable axes in other dimensions such as the rolling, pitching, and yawing axes in addition to the X-, Y-, and Z-axes. For the sake of simplicity, assume that in the following description, the support mechanism 32 supports the table top 31 so as to allow it to move along the X-, Y-, and Z-axes.

A position detection unit 35 is mounted on the bed driver 33. The position detection unit 35 repeatedly detects the position of the table top 31 in the XYZ space by using an existing position detection mechanism. As a position detection mechanism, a rotary encoder is typically used. The rotary encoder is mounted on the rotating shaft of the motor to output an electrical pulse every time the motor rotates through a predetermined angle. The rotary encoder is mounted on each motor, that is, each movable axis of the table top 31. The position detection unit 35 measures the position of the table top 31 relative to each movable axis based on an electrical pulse from each position detection mechanism. In this case, the position of the table top 31 will be simply referred to as a table top position. In addition, the table top position defined by the X-axis is called the X position, the table top position specified by the Y-axis is called the Y position (height), and the table top position specified by the Z-axis is called the Z position. The data of a measured table top position is supplied to the bed controller 34 and a storage controller 37.

The medical bed apparatus 30 is attached with a foot switch unit 36 including a plurality of foot switches which can be operated by the operator with his foot. An instruction signal corresponding to each pressed foot switch is supplied to the bed controller 34.

The storage controller 37 performs control to read and write table top position data from and to a storage unit 38 under the control of the bed controller 34. The storage unit 38 is a storage device built in the medical bed apparatus 30. The storage unit 38 mainly stores the table top position data supplied from the storage controller 37.

The bed controller 34 functions as the main unit of the medical bed apparatus 30. The bed controller 34 supplies a control signal to the bed driver 33 to move the table top 31 in accordance with a control signal from the gantry controller 16 or instruction signals from the foot switch unit 36 and the gantry operation panel unit 18. The bed controller 34 also controls the storage controller 37 in response to an ascending instruction issued via the foot switch unit 36 or the gantry operation panel unit 18, and causes the storage unit 38 to store the table top position at the time of the issuance of the ascending instruction as an automatic stop position (target return position) concerning the automatic return function. The bed controller 34 also controls the bed driver 33 in response to a descending instruction issued via the foot switch unit 36 or the gantry operation panel unit 18, and automatically places the table top 31 to the automatic storage position (target return position). The automatic return function will be described later.

As shown in FIG. 1, the console 50 is connected to the gantry 10. The console 50 functions as the main unit of the X-ray computed tomography apparatus. More specifically, the console 50 reconstructs CT image data based on raw data from the data acquisition unit 20. The console 50 displays the CT image data on a display device 70. The console 50 also controls the gantry controller 16 to execute X-ray CT imaging in accordance with the imaging conditions and imaging protocols input via the operation unit (not shown).

Figure 3:
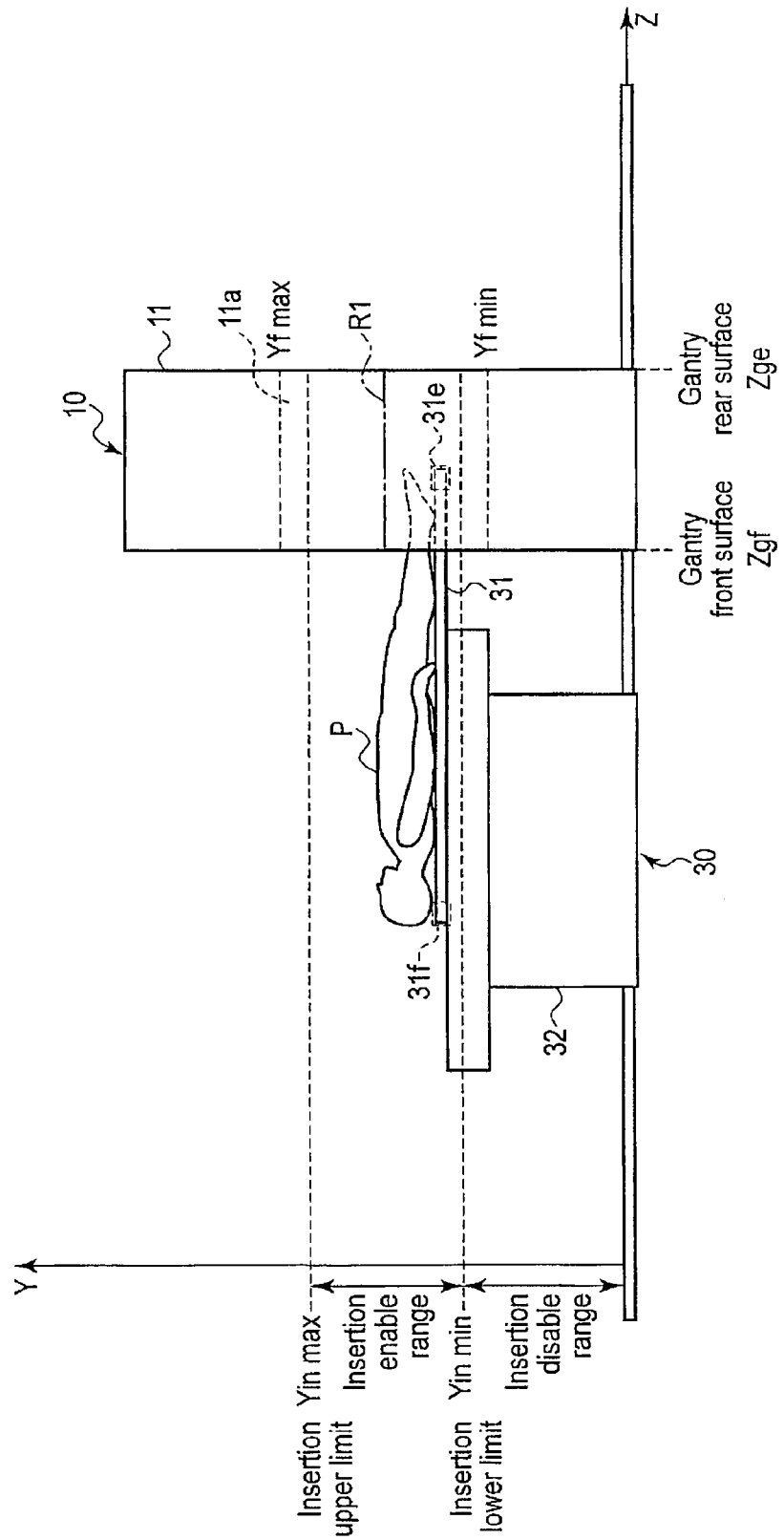
FIG. 3 is a side view of the gantry and medical bed apparatus in FIG. 1 when viewed from the X-axis direction.

An example of the operation of the X-ray computed tomography apparatus according to this embodiment will be described below. The positional relationship between the gantry 10 and the medical bed apparatus 30 will be described first with reference to FIGS. 3 and 4. FIG. 3 is a side view of the gantry 10 and medical bed apparatus 30 when viewed from the X-axis direction. FIG. 4 is a side view of the gantry 10 and medical bed apparatus 30 when viewed from the Z-axis direction. Let Yfmax be the height of the uppermost end of the bore 11a of the gantry housing 11, and Yfmin be the height of the lowermost end of the bore 11a. An insertion upper limit height Yinmax is the upper limit of height of the table top 31 which can be inserted into the bore 11a, and an insertion lower limit height Yinmin is the lower limit of height of the table top 31 which can inserted into the bore 11a. In this case, the height range of the table top 31 which can be inserted into the bore 11a corresponds to the interval between Yinmax and Yinmin. The maximum movable height of the table top 31 along the Y-axis can be set to any height as long as the body axis of a subject can be set to the height of the rotation axis R1. Typically, the maximum movable height of the table top 31 along the Y-axis is set to a height slightly lower than that of the rotation axis R1. Let Zgf be the position of the front surface of the gantry housing 11 relative to the Z-axis, and Zge be the position of the rear surface of the gantry housing 11 relative to the Z-axis. An end portion, of the end portion of the table top 31 in the Z direction, which is near to the gantry housing will be referred to as a depth-side end portion 31e, and an end portion far from the gantry housing 11 will be referred to as a front-side end portion 31f. If the depth-side end portion 31e is placed nearer to the front side than the front surface Zgf of the gantry housing 11, the table top 31 can descend to a position lower than the height Yinmin. If the table top 31 is placed at a position higher than the height Yinmin, the table top 31 can enter the bore 11a. That is, the height range lower than the height Yinmin is a height range in which the table top 31 cannot be inserted into the bore 11a, i.e., an insertion disable range.

The operation of the medical bed apparatus 30 according to this embodiment will be described next. The medical bed apparatus 30 has a manual operation function and an automatic operation function as operation functions associated with the movement of the table top 31. The manual operation function is a function of continuously moving the table top 31 in a predetermined direction while the operator presses a switch. In the manual operation function, the table top 31 does not stop unless the operator releases the switch. The automatic operation function is a function of moving the table top 31 to a target position, while the operator presses the switch, and automatically stopping the table top 31 when reaching the target position. In the automatic operation function, the table top 31 automatically stops when reaching the target position even if the operator presses the switch.

The manual operation function will be described in detail next. The manual operation function includes operation functions of, for example, ascending and descending the table top, inserting the table top, withdrawing the table top, and moving the table top to the right and left.

The ascending operation function is executed by pressing an ascending switch. While the operator presses the ascending switch, the bed controller 34 controls the bed driver 33 to ascend the table top 31 along the Y-axis at a constant speed or a variable speed. When the operator releases the ascending switch, the bed controller 34 controls the bed driver 33 to stop ascending the table top 31.

The descending operation function is executed by pressing a descending switch. While the operator presses the descending switch, the bed controller 34 controls the bed driver 33 to descend the table top 31 along the Y-axis at a constant speed or a variable speed. When the operator releases the descending switch, the bed controller 34 controls the bed driver 33 to stop descending the table top 31.

The inserting operation function is executed by pressing an insertion switch. While the operator presses the insertion switch, the bed controller 34 controls the bed driver 33 to slide the table top 31 along the Z-axis at a constant speed or a variable speed. When the operator releases the insertion switch, the bed controller 34 controls the bed driver 33 to stop sliding the table top 31.

The withdrawing operation function is executed by pressing a withdrawal switch. While the operator presses the withdrawal switch, the bed controller 34 controls the bed driver 33 to slide the table top 31 along the Z-axis at a predetermined speed or a variable speed. When the operator releases the withdrawal switch, the bed controller 34 controls the bed driver 33 to stop sliding the table top 31.

The rightward moving operation function is executed by pressing a rightward switch. While the operator switches the rightward switch, the bed controller 34 controls the bed driver 33 to slide the table top 31 to the right along the X-axis at a predetermined speed or a variable speed. When the operator releases the rightward switch, the bed controller 34 controls the bed driver 33 to stop sliding the table top 31.

The leftward moving operation function is executed by pressing a leftward switch. While the operator switches the leftward switch, the bed controller 34 controls the bed driver 33 to slide the table top 31 to the left along the X-axis at a predetermined speed or a variable speed. When the operator releases the leftward switch, the bed controller 34 controls the bed driver 33 to stop sliding the table top 31.

The automatic operation functions implemented in the medical bed apparatus 30 according to this embodiment include an automatic insertion function and an automatic return function.

The automatic insertion function is used before X-ray CT imaging. The automatic insertion function is a function of automatically moving the table top 31 from the patient placement position to the position set in the bore in advance (to be referred to as the target insertion position hereinafter). The height of the target insertion position is set to an arbitrary height between the insertion upper limit height and the insertion lower limit height. The automatic insertion function is executed by pressing an automatic insertion switch. While the operator presses the automatic insertion switch, the bed controller 34 controls the bed driver 33 to ascend the table top 31 along the Y-axis and slide the table top 31 in the forward direction along the Z-axis. When the table top 31 reaches the target insertion position, the bed controller 34 controls the bed driver 33 to automatically stop the table top 31. More specifically, when the table top 31 reaches the height of the target insertion position, the bed controller 34 controls the bed driver 33 to automatically stop ascending the table top 31. When the table top 31 reaches the Z position of the target insertion position, the bed controller 34 controls the bed driver 33 to automatically stop sliding the table top 31 in the forward direction. When the operator releases the automatic insertion switch before the table top 31 reaches the target insertion position, the bed controller 34 controls the bed driver 33 to stop ascending and sliding the table top 31.

The automatic return function is used after CT imaging. The automatic return function is a function of automatically moving the table top 31 from the imaging position in the bore 11a to the automatic stop position (to be referred to as the target return position hereinafter) outside the bore. As will be described later, the target return position is set to the position at which a patient can easily get out of the table top or can be easily gotten out of the table top. The automatic return function is executed by pressing an automatic return switch. More specifically, while the operator presses the automatic return switch, the bed controller 34 controls the bed driver 33 to slide the table top 31 in the backward direction along the Z-axis. When the depth-side end portion 31e of the table top 31 reaches the front surface position Zgf of the gantry housing 11, the bed controller 34 controls the bed driver 33 to descend the table top 31 along the Y-axis. When the table top 31 reaches the target return position, the bed controller 34 controls the bed driver 33 to automatically stop the table top 31. More specifically, when the table top 31 reaches the Z position of the target return position, the bed controller 34 controls the bed driver 33 to automatically stop sliding the table top 31 in the backward direction. When the table top 31 reaches the height of the target return position, the bed controller 34 controls the bed driver 33 to automatically stop descending the table top 31. When the operator releases the automatic return switch before the table top 31 reaches the automatic stop position, the bed controller 34 controls the bed driver 33 to stop descending and sliding the table top 31. Note that the operation of the table top 31 in the automatic return function is not limited to this. For example, while the operator presses the automatic return switch, the bed controller 34 may control the bed driver 33 to slide the table top 31 in the backward direction along the Z-axis while descending the table top 31 along the Y-axis to the insertion lower limit height. When the table top 31 reaches the insertion lower limit height, the bed controller 34 controls the bed driver 33 to automatically stop descending the table top 31 and continuously slide the table top 31 in the backward direction along the Z-axis. When the depth-side end portion 31e of the table top 31 reaches the front surface position Zgf of the gantry housing 11, the bed controller 34 controls the bed driver 33 to descend the table top 31 along the Y-axis and continuously slide the table top 31 in the backward direction along the Z-axis. When the table top 31 reaches the target return position, the bed controller 34 controls the bed driver 33 to automatically stop the table top 31.

The gantry operation panel unit 18 is provided with the ascending switch, descending switch, insertion switch, withdrawal switch, rightward moving switch, leftward moving switch, automatic insertion switch, and automatic return switch. As described above, the foot switch unit 36 typically includes two foot switches to which the operator can arbitrarily assign functions. The operator can assign arbitrary functions of the ascending operation function, descending operation function, insertion operation function, withdrawal operation function, rightward moving operation function, leftward moving operation function, automatic insertion function, and automatic return function to the respective foot switches mounted on the foot switch unit 36. In order to make the foot switch unit 36 implement both the placement of the table top 31 in the bore 11a and the placement of the table top 31 at a patient get out position, it is preferable to assign the automatic insertion switch and the automatic return switch to the two foot switches. Note that the number of foot switches mounted on the foot switch unit 36 is not limited to two. One foot switch or three or more foot switches may be mounted on the foot switch unit 36.

The automatic return function will be described in detail next. As described above, the automatic return function is a function of automatically placing the table top 31 at a target return position. The height of the target return position is initially set to a preset default value. After the automatic return function places the table top 31 at the target return position, the operator needs to place the table top 31 at the height at which each patient can easily get out of the table top (or can be easily gotten out of the table top) by operating manual operation switches such as the ascending switch, descending switch, insertion switch, withdrawal switch, rightward moving switch, and leftward moving switch.

The present inventor has found an empirical rule that the height of the table top 31 at which a patient rides on it is almost equal to the height of the table top 31 at which the patient gets out of it. The X-ray computed tomography apparatus according to this embodiment automatically stops the table top 31 at a proper height corresponding to each patient after X-ray CT imaging based on this empirical rule without mounting any additional device such as a special sensor or interface.

The following will describe routine operation at the time of CT imaging in the X-ray computed tomography apparatus according to this embodiment.

Figure 5:
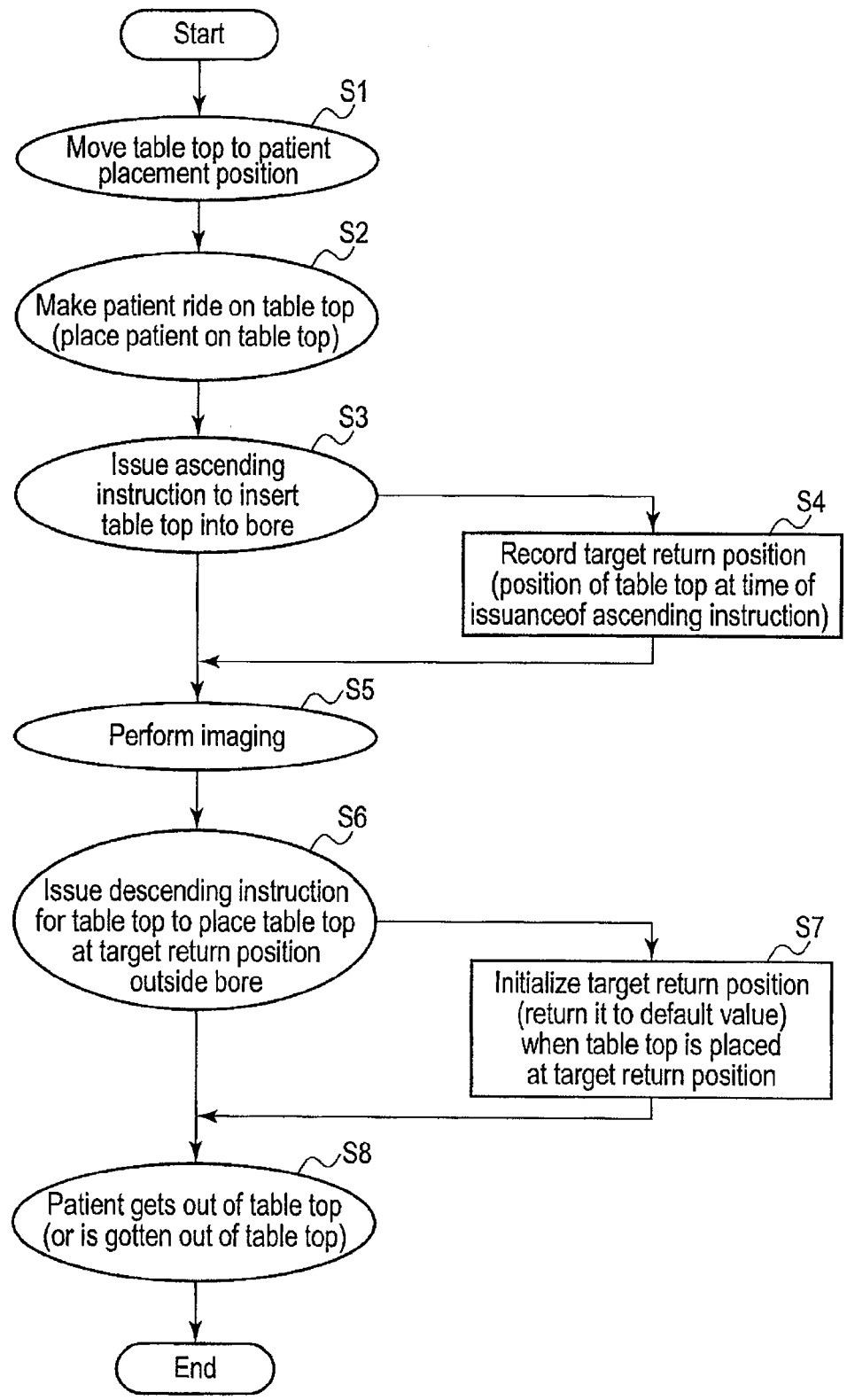
FIG. 5 is a flowchart for explaining a typical procedure for routine operation in a CT examination using the X-ray computed tomography apparatus in FIG. 1.

FIG. 5 is a flowchart for explaining a typical procedure for routine operation in CT examination using the X-ray computed tomography apparatus according to this embodiment. Before X-ray CT imaging, the table top 31 is placed at the initial position. The initial position is, for example, a table top position at the end time of the previous X-ray CT imaging. Therefore, the initial position is not sometimes the height at which a patient subjected to the current X-ray CT imaging can easily get out of the table top (or can be easily gotten out of the table top). As shown in FIG. 5, before X-ray CT imaging, the operator operates manual operation switches such as the ascending switch and descending switch to move the table top 31 from the initial position and place the table top 31 at a patient placement position suitable for the patient subjected to the current X-ray CT imaging (step S1). A patient placement position is not a parameter set in the medical bed apparatus. The operator subjectively determines a height at which the patient can easily get out of the table top (or can be easily gotten out of the table top) by observing the shape, height, condition, and the like of the patient. If, for example, the patient is an ordinary adult male, the patient walks into the CT imaging room and rides on the table top 31 by himself. In this case, the operator manually descends the table top 31 to the height at which the ordinary male patient can easily sit on the table top. If the patient is a child or short elderly person, the operator descends the table top 31 to a height lower than that for ordinary males. When the patient enters the CT imaging room with the help of the operator or the like or on a stretcher, the operator ascends the table top 31 to the height at which the table top can be inserted into the bore 11a, more specifically, a height slightly higher than the height at which the table top 31 can be inserted into the bore 11a.

When the table top 31 is placed at the patient placement position, the patient rides or is made to ride on the table top 31 (step S2). When the patient completely rides on the table top 31, the operator issues an instruction to ascend the table top 31 via the foot switch unit 36 or the gantry operation panel unit 18 so as to insert the table top 31 into the bore 11a (step S3).

Means for inserting the table top 31 into the bore 11a include manual operation and an automatic insertion function. When performing manual operation, the operator inserts the table top 31 to an arbitrary position in the bore 11a by mainly operating the ascending switch and the insertion switch as needed. More specifically, first of all, the operator presses the ascending switch. While the operator presses the ascending switch, the bed controller 34 controls the bed driver 33 to ascend the table top 31. If the operator determines that the table top 31 has ascended to the insertion lower limit height, he/she presses the insertion switch in addition to the ascending switch. While the operator presses the insertion switch, the bed controller 34 controls the bed driver 33 to slide the table top 31 in the forward direction. If the operator determines that the height of the body axis of the patient has coincided with the height of the rotation axis R1, he/she releases the ascending switch. When the operator releases the ascending switch, the bed controller 34 controls the bed driver 33 to stop the table top 31. If the operator determines that the table top 31 has been inserted into the bore 11a, he/she releases the insertion switch. When the operator releases the insertion switch, the bed controller 34 controls the bed driver 33 to stop the table top 31. When using the automatic insertion function, the operator presses the automatic insertion switch. While the operator presses the automatic insertion switch, the bed controller 34 controls the bed driver 33 to ascend the table top 31 along the Y-axis and slide the table top 31 in the forward direction along the Z-axis. While the table top 31 is moved, the position detection unit 35 repeatedly detects the table top position. The bed controller 34 monitors the table top position detected by the position detection unit 35 and detects that the table top 31 reaches the target insertion position. Upon detecting that the table top 31 has reached the target insertion position, the bed controller 34 controls the bed driver 33 to automatically stop the table top 31.

Subsequently, the operator finely adjusts the table top position by manual operation so as to align the center of an imaging region of the subject with the imaging center (isocenter) of the bore. Note that before completely inserting the table top 31 into the bore 11a, the operator sometimes temporarily stops the table top 31 at an insertion enable height to check the fixing tools for a patient or secure a route for a contrast agent.

As described above, when moving the table top 31 from the patient placement position into the bore 11a, the operator issues an ascending instruction for the table top 31 by operating the ascending switch or the automatic insertion switch. When an ascending instruction is issued, the storage controller 37 causes the storage unit 38 to store, as a target return position, the table top position at the time of the issuance of the ascending instruction (step S4). That is, the target return position is set to the height of the table top 31 when the patient rides on the table top 31 or is made to ride on the table top 31. Note that a target return position setting algorithm will be described in detail later.

It is preferable to store, as a target return position, the height, Z position, and X position of the table top 31 at the time of the issuance of an ascending instruction for the table top 31 in association with each other. Note that a target return position in this embodiment may have at least the dimension of height (Y dimension), and the Z and X dimensions may be set to default values instead of Z and X positions at the time of the issuance of an ascending instruction. If the Z position of the target return position is set to a default value, the default value of the Z position or the Z position of the target return position may be set to the limit value of the movable range of the table top 31 in the backward direction. When setting the X position of the target return position to a default value, it is preferable to set the default value of the X position to the center X position (the X position of the isocenter). Alternatively, a target return position may be associated with the tilt angle of the rotating ring 12 or the Z position of the gantry housing 11 at the time of the issuance of an ascending instruction. For the sake of simplicity, assume that in the following description, values in dimensions other than the height of the patent placement position are default values. That is, for the sake of simplicity, assume that in the following description, the height of the target return position is the height of the table top 31 when the patient rides on it (or is made to ride on it), and values in other dimensions are set to default values.

When the patient is completely placed in the bore 11a, the operator presses the imaging start button mounted on the gantry operation panel unit 18 or the like. When the operator presses the imaging start button, the gantry 10 executes X-ray CT imaging (step S5). At the time of X-ray CT imaging, the X-ray tube 13 repeatedly emits X-rays while the rotating ring 12 rotates about the rotation axis R1. The rotating ring 12 may tilt relative to the vertical axis, as needed. The data acquisition unit 20 acquires raw data associated with the subject from the X-ray detector 14. The acquired raw data is transmitted to the console 50. The console 50 reconstructs CT image data based on the raw data. The display device 70 displays the CT image data.

After the completion of X-ray CT imaging, the operator issues an instruction to descend the table top 31 via the foot switch unit 36 or the gantry operation panel unit 18 to move the table top 31 from inside the bore 11a to the target return position outside the bore 11a (step S6).

Methods of placing the table top 31 at a target return position include a method using manual descending operation and a method using the automatic return function. When using manual descending operation, the operator places the table top 31 at the target return position outside the bore 11a by mainly operating the descending switch and the withdrawal switch as needed. More specifically, first of all, the operator simultaneously presses the withdraw switch and the descending switch after X-ray CT imaging. While the operator presses the descending switch, the bed controller 34 controls the bed driver 33 to descend the table top 31. The bed controller 34 monitors the table top position repeatedly detected by the position detection unit 35 to detect that the table top 31 has reached the insertion lower limit height. Upon detecting that the table top 31 has reached the insertion lower limit height, the bed controller 34 controls the bed driver 33 to automatically stop the table top 31. While the operator presses the withdrawal switch, the bed controller 34 controls the bed driver 33 to slide the table top 31 in the backward direction along the Z-axis. Upon determining that the depth-side end portion of the table top 31 has sufficiently separated from the front surface of the gantry housing 11, the operator releases the withdrawal switch. When the operator releases the withdrawal switch, the bed controller 34 controls the bed driver 33 to stop the table top 31. The bed controller 34 also monitors the table top position repeatedly detected by the position detection unit 35 during the movement of the table top 31 along the Z-axis to detect that the depth-side end portion 31e of the table top 31 reaches the front surface position Zgf of the gantry housing 11. Upon detecting that the depth-side end portion 31e has reached the front surface position Zgf, the bed controller 34 controls the bed driver 33 to descend the table top 31 along the Y-axis and continuously slide the table top 31 in the backward direction along the Z-axis. When the table top 31 has reached the target return position, the bed controller 34 controls the bed driver 33 to automatically stop the table top 31.

When using the automatic return function, the operator presses the automatic return switch after X-ray CT imaging. While the operator presses the automatic return switch, the bed controller 34 monitors the table top position detected by the position detection unit 35 to detect that the depth-side end portion of the table top 31 reaches the front surface position of the gantry housing 11. When the depth-side end portion of the table top 31 reaches the front surface position of the gantry housing 11, the bed controller 34 controls the bed driver 33 to continuously slide the table top 31 in the backward direction along the Z-axis and descend the table top 31 along the Y-axis. When the table top 31 has reached the target return position, the bed controller 34 controls the bed driver 33 to automatically stop the table top 31.

When the table top 31 is placed at the target return position, the storage controller 37 initializes the target return position in accordance with the algorithm described later (step S7). That is, the target return position is returned to a default value.

When the table top 31 is placed at the target return position, the patient gets out of the table top 31 by himself or is gotten out of the table top 31 with the help of the operator or the like (step S8).

As described above, this embodiment can automatically place the table top 31 at the height at which each patient can easily get out of the table top (or can be easily gotten out of the table top), by only making the operator keep pressing the descending switch or the automatic return switch. Therefore, the embodiment can easily move the table top 31 to the height at which the patient can easily get out of the table top (or can be easily gotten out of the table top) as compared with the prior art. This allows the operator to concentrate on operation other than moving the table top 31, e.g., giving care to the patient.

Figure 6:
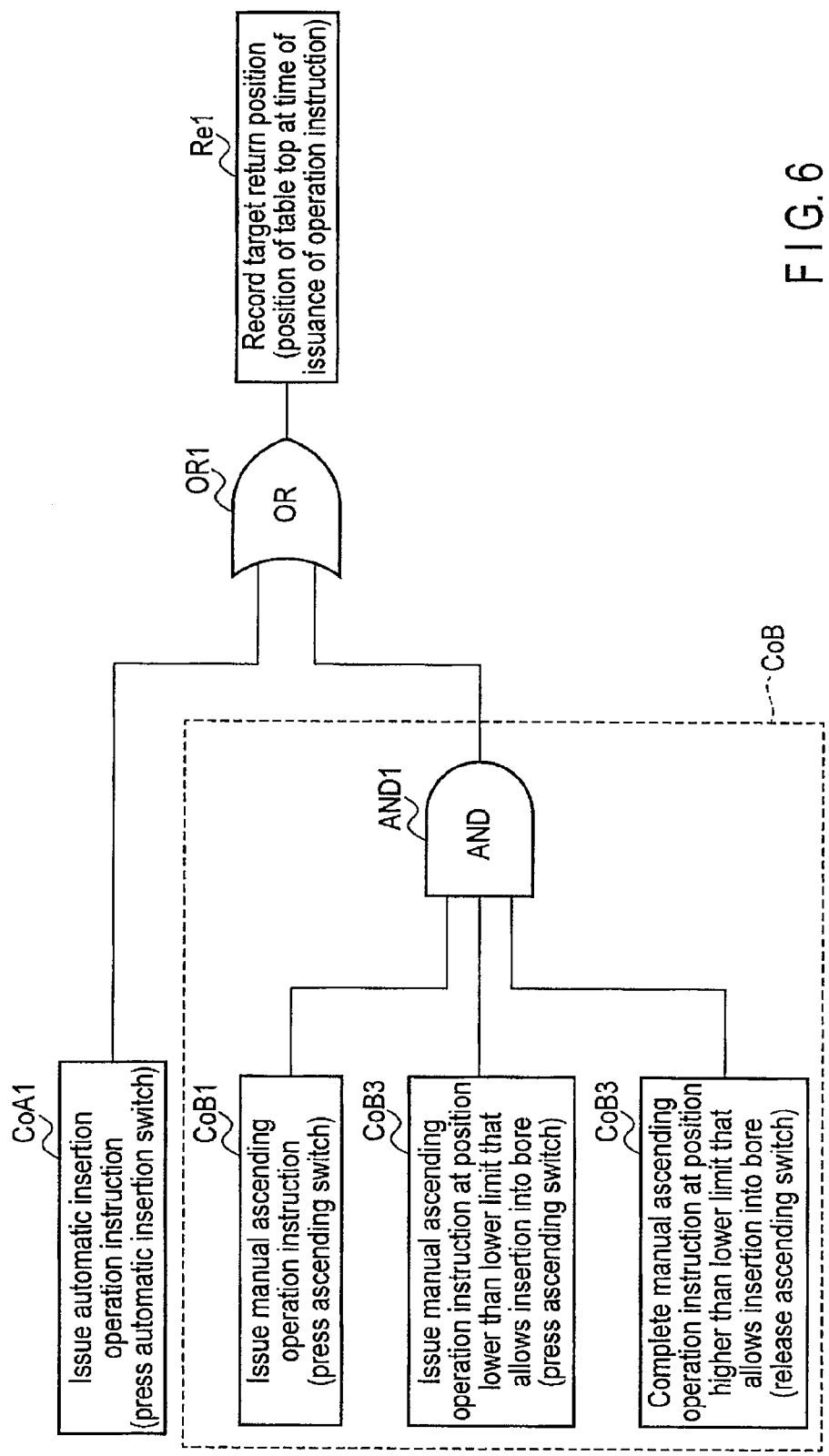
FIG. 6 is a view showing a target return position setting algorithm executed by a storage controller in step S4 in FIG. 5.

This is the end of the description of a procedure for routine operation in CT examination by the X-ray computed tomography apparatus according to this embodiment. A target return position setting algorithm executed by the storage controller 37 in step S4 will be described in detail next. FIG. 6 is a view showing a target return position setting algorithm by the storage controller 37. As shown in FIG. 6, the target return position setting algorithm includes a determination condition CoA associated with the operation of the automatic insertion switch and a determination condition CoB associated with the operation of the ascending switch. If at least one of the determination condition CoA and the determination condition CoB is satisfied (OR1: true), the storage controller 37 stores the table top position at the time of the issuance of an operation instruction as a target return position. If neither the determination condition CoA nor the determination condition CoB is satisfied (OR1: false), the storage controller 37 does not store the table top position at the time of the issuance of an operation instruction as a target return position, and sets a default value as a target return position.

The determination condition CoA associated with the operation of the automatic insertion switch includes only a determination condition CoA1. The determination condition CoA holds true when an automatic insertion operation instruction is issued, and holds false when no automatic insertion operation instruction is issued. More specifically, when the operator presses the automatic insertion switch, the storage controller 37 determines that the determination condition CoA1 is satisfied (true). In this case, since at least one of the determination condition CoA and the determination condition CoB is satisfied (OR1: true), the storage controller 37 stores, as a target return position, the table top position detected by the position detection unit 35 at the time of the issuance of an automatic insertion operation instruction. That is, the table top position detected by the position detection unit 35 at the time of the issuance of the automatic insertion operation instruction is set as a target return position.

The determination condition CoB associated with the ascending switch includes a determination condition CoB1, a determination condition CoB2, and a determination condition CoB3. The determination condition CoB1 holds true when a manual ascending operation instruction is issued, and holds false when no manual ascending operation instruction is issued. More specifically, when the operator presses the ascending switch, the storage controller 37 determines that the determination condition CoB1 is satisfied (true). When the operator does not press the ascending switch, the storage controller 37 determines that the determination condition CoB1 is not satisfied (false). The determination condition CoB2 holds true if the table top position at the time of the issuance of a manual ascending operation instruction is lower than the lower limit height allowing insertion into the bore 11a (insertion lower limit height), and holds false if the table top position is higher than the insertion lower limit height. More specifically, if the table top position at the time of pressing the ascending switch is lower than the insertion lower limit height, the storage controller 37 determines that the condition CoB2 is satisfied (true). If the table top position at the time of pressing the ascending switch is higher than the insertion lower limit height, the storage controller 37 determines that the condition CoB2 is not satisfied (false). The determination condition CoB3 holds true when the table top position at the time of the completion of a manual ascending operation instruction is higher than the insertion lower limit height, and holds false when the table top position is lower than the insertion lower limit height. More specifically, if the table top position at the time of releasing the ascending switch is higher than the insertion lower limit height, the storage controller 37 determines that the condition CoB3 is satisfied (true). If the table top position at the time of releasing the ascending switch is lower than the insertion lower limit height, the storage controller 37 determines that the condition CoB3 is not satisfied (false).

If all the conditions CoB1, CoB2, and CoB3 are satisfied (AND1: true), since at least one of the determination condition CoA and the determination condition CoB is satisfied (OR1: true), the storage controller 37 stores, as a target return position, the table top position detected by the position detection unit 35 at the time of the issuance of an automatic insertion operation instruction.

The following will describe a procedure for the operation of the storage controller 37 when using a setting algorithm associated with manual ascending operation. Every time the operator presses the ascending switch, the storage controller 37 causes the storage unit 38 to store the table top position at the time of pressing the ascending switch. The storage controller 37 then determines whether the height of the table top position at the time of pressing the ascending switch is lower than the insertion lower limit height, i.e., the determination condition CoB2 is satisfied. Upon determining that the condition CoB2 is not satisfied, the storage controller 37 erases the data of the table top position stored in the storage unit 38. Upon determining that the condition CoB2 is satisfied, the storage controller 37 causes the storage unit 38 to hold the data of the table top position. The storage controller 37 then waits until the operator releases the ascending switch. When the operator releases the ascending switch, the storage controller 37 determines whether the table top position at the time of releasing the ascending switch is higher than the insertion lower limit height, i.e., the condition Co3 is satisfied. Upon determining that the condition CoB3 is not satisfied, the storage controller 37 erases the data of the table top position stored in the storage unit 38. Upon determining that the condition CoB3 is satisfied, the storage controller 37 causes the storage unit 38 to store the stored table top position as a target return position.

As described above, the storage controller 37 does not immediately set the table top position at the time of pressing the ascending switch as a target return position. This is because the following two operations are frequently performed before X-ray CT imaging. The first factor is that the operator sometimes finely adjusts the table top position to place the table top 31 at a table top placement position in accordance with the height and the like of a patient. In this case, the operator presses or releases the ascending switch at a position lower than the insertion lower limit height. The second factor is that the operator sometimes finely adjusts the table top position to place the table top 31 at the imaging position. In this case, the operator presses or releases the ascending switch at a position higher than the insertion lower limit height. These heights of the table top positions at the time of pressing the ascending switch for fine adjustment are not the heights at which the patient can easily get out of the table top or can be easily gotten out of the table top. The conditions CoB2 and CoB3 described above are provided to inhibit the height of the table top position at the time of pressing the ascending switch for such fine adjustment from being set as a target return position.

If X-ray CT imaging starts without satisfaction of the condition ADN1 or condition OR1 described above, the storage controller 37 sets a default value as a target return position.

As described above, the table top position is finely adjusted to place the table top 31 at the patient placement position. The table top position is sometimes finely adjusted by operating not only the ascending switch and the descending switch but also the automatic insertion switch. Assume that the setting algorithm in FIG. 6 is executed. In this case, even if the operator presses the automatic insertion switch for fine adjustment, the table top position at the time of pressing the automatic insertion switch is stored as a target return position. The table top position at the time of pressing the automatic insertion switch for fine adjustment is not the height at which the patient rides on the table top 31 (or is made to ride on the table top), and hence is not the position at which the patient can easily get out of the table top 31 (or can be easily gotten out of the table top). In order to prevent this, the storage controller 37 may execute a setting algorithm more robust than the target return position setting algorithm in FIG. 6.

FIG. 7 shows another target return position setting algorithm executed by the storage controller 37 in step S4 in FIG. 5. The setting algorithm shown in FIG. 7 is obtained by adding a determination condition CoA2 to the setting algorithm in FIG. 6. The determination condition CoA2 holds true when the table top position at the time of the completion of an automatic insertion operation instruction is higher than the insertion lower limit height, and holds false if the table top position is lower than the insertion lower limit height. More specifically, if the table top position at the time of releasing the automatic insertion switch is higher than the insertion lower limit height, the storage controller 37 determines that the condition CoA2 is satisfied (true). If the table top position at the time of releasing the automatic insertion switch is lower than the insertion lower limit height, the storage controller 37 determines that the condition CoA2 is not satisfied (false). If both the determination condition CoA1 and the determination condition CoA2 are satisfied (AND2: true), since at least one of the determination condition CoA and the determination condition CoB is satisfied (OR1: true), the storage controller 37 stores, as a target return position, the table top position detected by the position detection unit 35 at the time of the issuance of an automatic insertion operation instruction.

The following will describe a procedure for the operation of the storage controller 37 when using the setting algorithm associated with the automatic insertion function in FIG. 7. Every time the operator presses the automatic insertion switch, the storage controller 37 causes the storage unit 38 to store the table top position at the time of pressing the automatic insertion switch. The storage controller 37 then waits until the operator releases the automatic insertion switch. When the operator releases the automatic insertion switch, the storage controller 37 determines whether the height of the table top position at the time of releasing the automatic insertion switch is higher than the insertion lower limit height. That is, the storage controller 37 determines whether the determination condition CoA2 is satisfied. Upon determining that the determination condition CoA2 is not satisfied, the storage controller 37 erases the data of the table top position stored in the storage unit 38. Upon determining that the determination condition CoA2 is satisfied, the storage controller 37 causes the storage unit 38 to store the stored table top position as a target return position.

As described above, with the setting algorithm associated with the automatic insertion function in FIG. 7, when the operator releases the automatic insertion switch at a position lower than the insertion lower limit height, the storage controller 37 erases the data of the table top position at the time of pressing the automatic insertion switch from the storage unit 38. The storage controller 37 can therefore prevent the table top position at the time of pressing the automatic insertion switch for the fine adjustment of the table top 31 from being stored as a target return position.

This is the end of the description of the target return position storage algorithm executed by the storage controller 37 in step S4 in FIG. 5.

The target return position erase algorithm executed by the storage controller 37 in step S7 in FIG. 5 will be described next. FIG. 8 shows the target return position erase algorithm. As shown in FIG. 8, the target return position erase algorithm includes a determination condition CoC associated with the operation of the automatic return switch and a determination condition CoD associated with the operation of the descending switch. If at least one of the determination condition CoC and the determination condition CoD is satisfied (OR2: true), the storage controller 37 erases the data of the target return position from the storage unit 38. If neither the determination condition CoC nor the determination condition CoD is satisfied, the storage controller 37 causes the storage unit 38 to keep storing the data of the target return position without erasing it.

The determination condition CoC associated with the operation of the automatic return switch includes a determination condition CoC1 and a determination condition CoC2. The determination condition CoC1 holds true when an automatic return operation instruction is issued, and holds false when no automatic return operation instruction is issued. More specifically, when the operator presses the automatic return switch, the storage controller 37 determines that the condition CoC1 is satisfied (true). When the operator does not press the automatic return switch, the storage controller 37 determines that the condition CoC1 is not satisfied (false). The determination condition CoC2 holds true when the table top 31 automatically stops at the automatic return position, and holds false when the table top 31 does not automatically stop at the automatic return position. If both the determination condition CoC1 and the determination condition CoC2 are satisfied (AND3: true), since at least one of the determination condition CoC and the determination condition CoD is satisfied (OR2: true), the storage controller 37 erases the data of the target return position from the storage unit 38.

The determination condition CoD associated with the operation of the descending switch includes a determination condition CoD1 and a determination condition CoD2. The determination condition CoD1 holds true when a manual descending operation instruction is issued, and holds false when no manual descending operation instruction is issued. More specifically, when the operator presses the descending switch, the storage controller 37 determines that the condition CoD1 is satisfied (true). When the operator does not press the descending switch, the storage controller 37 determines that the condition CoD1 is not satisfied (false). The determination condition CoD2 holds true when the table top 31 automatically stops at the automatic return position, and holds false when the table top 31 does not automatically stop at the automatic return position. If both the determination condition CoD1 and the determination condition CoD2 are satisfied (AND4: true), since at least one of the determination condition CoC and the determination condition CoD is satisfied (OR2: true), the storage controller 37 erases the data of the target return position from the storage unit 38.

The following will describe a procedure for the operation of the storage controller 37 using an erase algorithm associated with the operation of the automatic return switch. After X-ray CT imaging, the operator presses the automatic return switch or the manual descending switch. The storage controller 37 monitors the table top position repeatedly detected by the position detection unit 35 to detect that the bed controller 34 automatically stops the table top 31 when it reaches the target return position. Upon detecting that the table top 31 has stopped at the target return position, the storage controller 37 erases the data of the target return position from the storage unit 38 (Re2). Thereafter, the storage controller 37 sets the target return position to a default value.

If the apparatus terminates X-ray CT examination without satisfying the condition AND3, condition AND4, or condition OR2, the storage controller 37 sets a default value as a target return value.

The table top 31 may stop before it reaches the target return position, and the patient may get out of the table top 31 or be gotten out of the table top 31. In this case, since the patient is not placed on the table top 31, the target return position should be erased from the storage unit 38. According to the above erase algorithm, however, when the table top 31 stops before it reaches the target return position, the data of the target return position is kept stored without being erased from the storage unit 38. In order to cope with such an event, the storage controller 37 may execute an erase algorithm more robust than the erase algorithm in FIG. 8.

Figure 9:
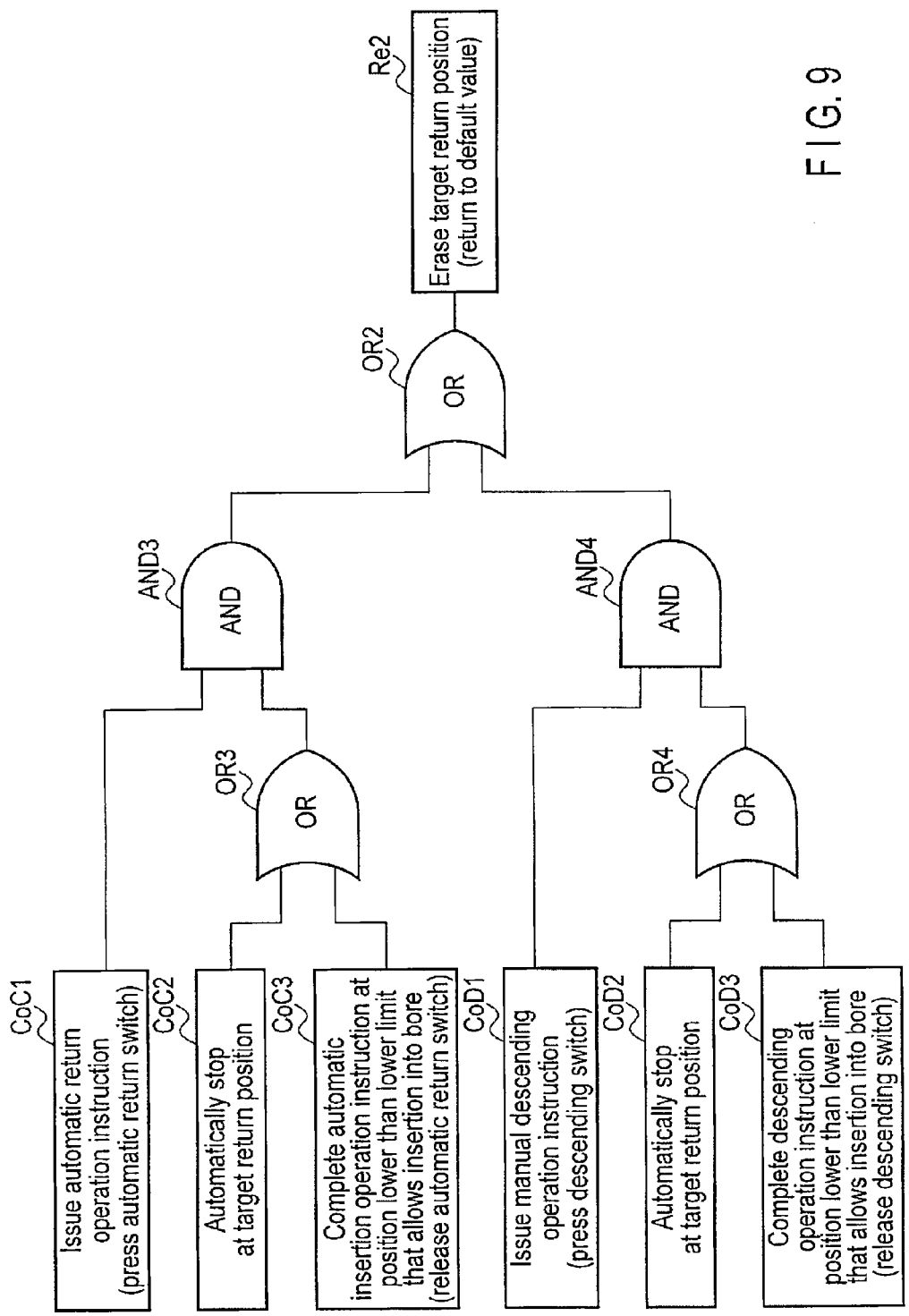
FIG. 9 is a view showing another target return position erase algorithm executed by the storage unit in step S7 in FIG. 5.

FIG. 9 is a view showing another target return position erase algorithm executed by the storage controller 37 in step S7 in FIG. 5. The erase algorithm in FIG. 9 is obtained by adding a determination condition CoC3 and a determination condition CoD3 to the erase algorithm in FIG. 8.

The determination condition CoC3 holds true when the table top position at the time of the completion of an automatic return operation instruction is lower than the insertion lower limit height, and holds false when the table top position is higher than the insertion lower limit height. More specifically, if the table top position at the time of releasing the automatic return switch is lower than the insertion lower limit height, the storage controller 37 determines that the determination condition CoC3 is satisfied (true). If the table top position at the time of releasing the automatic return switch is higher than the insertion lower limit height, the storage controller 37 determines that the determination condition CoC3 does not hold (false). If at least one of the determination condition CoC2 and the determination condition CoC3 is satisfied (OR3; true), since at least one the determination condition CoC and the determination condition CoD is satisfied (OR2: true), the storage controller 37 erases the data of the target return position from the storage unit 38.

The determination condition CoD3 holds true when the table top position at the time of the completion of a manual descending operation instruction is lower than the insertion lower limit height, and holds false when the table top position is higher than the insertion lower limit height. More specifically, if the table top position at the time of releasing the descending switch is lower than the insertion lower limit height, the storage controller 37 determines that the determination condition CoD3 is satisfied (true). If the table top position at the time of releasing the descending switch is higher than the insertion lower limit height, the storage controller 37 determines that the condition CoD3 is not satisfied (false). If at least one of the determination condition CoD2 and the determination condition CoD3 is satisfied (OR4: true), since at least one of the determination condition CoC and the determination condition CoD is satisfied (OR2: true), the storage controller 37 erases the data of the target return position from the storage unit 38.

As described above, with the erase algorithm associated with the automatic return function in FIG. 9, the storage controller 37 erases the data of the target return position from the storage unit 38 even when a descending operation instruction is complete at a position lower than the insertion lower limit height. The storage controller 37 can therefore prevent the target return position from being kept stored in the storage unit 38 when the table top 31 stops before it reaches the target return position.

This is the end of the description of the target return position erase algorithm executed by the storage controller 37 in step S7 in FIG. 5.

According to the above description, the image diagnostic apparatus according to this embodiment includes the table top 31, the support mechanism 32, the bed driver 33, the ascending instruction switch, the descending instruction switch, the storage unit 38, and the bed controller 34. A subject is placed on the table top 31. The support mechanism 32 movably supports the table top 31. The bed driver 33 generates driving power to be supplied to the support mechanism 32 to move the table top 31. The imaging mechanism 10 includes a mechanism for acquiring the medical image data associated with the subject placed on the table top 31. The ascending instruction switch receives an ascending instruction for the table top 31. The descending instruction switch receives a descending instruction for the table top 31. The ascending instruction switch and the descending instruction switch are mounted on at least one of the gantry operation panel unit 18 and the foot switch unit 36. The storage unit 38 stores the height of the table top 31 at the time of the issuance of an ascending instruction as a target return position. Upon issuance of a descending instruction, the bed controller 34 controls the bed driver 33 to descend the table top 31 to the target return position stored in the storage unit 38.

With the above arrangement, the storage unit 38 can store, as a target return position, the height of the table top 31 at the time point when a subject rides on the table top 31 by itself (or is made to ride on the table top 31). As described above, a target return position is at a height optical for each patient in accordance with, for example, his/her shape and condition. When the operator issues a descending instruction, the bed controller 34 moves the table top 31 to this target return position. Therefore, the subject can get out of the table top (or can be gotten out of the table top) at the same height as that when the subject has ridden on the table top 31 (or has been made to ride on the table top 31). According to this embodiment, the operator can place the table top 31 at the height at which a subject can easily get out of the table top (or can be easily gotten out of the table top) by one-touch operation without finely adjusting the table top position. In addition, the storage unit 38 can store, as a target return position, the height of the table top 31 at the time of the issuance of an ascending instruction, which is generally issued, to insert the table top 31 into the bore 11a. That is, the embodiment has an algorithm which can store the height of the table top 31 without requesting the operator to store the height of the table top 31. In addition, as described above, the embodiment does not require any hardware such as a special sensor or interface for implementing this effect. The embodiment can therefore place the table top 31 at a height suitable for each patient with an inexpensive arrangement.

This embodiment can therefore provide an image diagnostic apparatus, X-ray computed tomography apparatus, medical bed apparatus, and bed control method which can reduce the operator's trouble of moving the table top after imaging operation.

Note that in this embodiment, the bed controller 34, the storage controller 37, and the storage unit 38 are mounted on the medical bed apparatus 30. However, the embodiment is not limited to this. For example, the bed controller 34, the storage controller 37, and the storage unit 38 may be provided on the imaging mechanism 10 or the console 50.

The invention claimed is:

1. An image diagnostic apparatus, comprising:
   a table top for a subject;
   a support mechanism configured to movably support the table top;
   a driving power generator configured to generate driving power to be supplied to the support mechanism to move the table top;
   an imaging mechanism configured to acquire medical image data associated with the subject placed on the table top;
   a first operation unit configured to receive an ascending instruction for the table top;
   a second operation unit configured to receive a descending instruction for the table top;
   a storage unit configured to store a height of the table top at a time of issuance of the ascending instruction; and
   a movement controller configured to control the driving power generator to descend the table top to the stored height upon issuance of the descending instruction.

2. The image diagnostic apparatus of claim 1, wherein the ascending instruction includes an instruction for ascending the table top along a vertical axis, and
   the apparatus further comprises a storage controller configured to cause the storage unit to store an ascent-start-height at the time of issuance of the ascending instruction every time the ascending instruction is issued,
   wherein the storage controller causes the storage unit to store the ascent-start-height as the stored height if the ascent-start-height is lower than a lower limit height at which the table top is configured to be inserted into a bore of the imaging mechanism and an ascent-completion-height at which the table top stops to ascend at the time of completion of the ascending instruction is higher than the lower limit height, and erases the ascent-start-height stored in the storage unit if the ascent-start-height is higher than the lower limit height or the ascent-completion-height is lower than the lower limit height.

3. The image diagnostic apparatus of claim 1, wherein the ascending instruction includes instructions to ascend and slide the table top to automatically move the table top to a predetermined position in a bore of the imaging mechanism, and
   the apparatus further comprises a storage controller configured to cause the storage unit to store, as the stored height, an ascent-start-height from which the table top starts to ascend at the time of issuance of the ascending instruction.

4. The image diagnostic apparatus of claim 3, wherein the storage controller causes the storage unit to store, as the stored height, the ascent-start-height if an ascent-completion-height at which the table top stops to ascend at the time of completion of the ascending instruction is higher than the lower limit height at which the table top is configured to be inserted into the bore, and erases the ascent-start-height stored in the storage unit if the ascent-completion-height is lower than the lower limit height.

5. The image diagnostic apparatus of claim 1, wherein the storage unit stores, in addition to the stored height, a position of the table top along a moving axis other than the vertical axis at the time of issuance of the ascending instruction, and
   the movement controller controls the driving power generator upon issuance of the descending instruction to descend the table top to the stored height and move the table top to the position along the moving axis other than the vertical axis.

6. An X-ray computed tomography apparatus comprising:
   a table top for a subject;
   a support mechanism configured to movably support the table top;
   a driving power generator configured to generate driving power to be supplied to the support mechanism to move the table top;
   an X-ray tube configured to generate X-rays;
   an X-ray detector configured to detect X-rays generated from the X-ray tube;
   a gantry on which the X-ray tube and the X-ray detector are mounted and which includes a bore into which the table top is inserted;
   a first operation unit configured to receive an ascending instruction for the table top;
   a second operation unit configured to receive a descending instruction for the table top;
   a storage unit configured to store a height of the table top at a time of issuance of the ascending instruction; and
   a movement controller configured to control the driving power generator to descend the table top to the stored height upon issuance of the descending instruction.

7. A medical bed apparatus, comprising:
   a table top for a subject;
   a support mechanism configured to movably support the table top;
   a driving power generator configured to generate driving power to be supplied to the support mechanism to move the table top;
   a first operation unit configured to receive an ascending instruction for the table top;
   a second operation unit configured to receive a descending instruction for the table top;
   a storage unit configured to store a height of the table top at a time of issuance of the ascending instruction; and a movement controller configured to control the driving power generator to descend the table top to the stored height upon issuance of the descending instruction.

8. A control method for a medical bed apparatus including a table top for a subject, a support mechanism configured to movably support the table top, a driving power generator configured to generate driving power to be supplied to the support mechanism to move the table top, a first operation unit configured to receive an ascending instruction for the table top, a second operation unit configured to receive a descending instruction for the table top, and a storage unit configured to store a height of the table top at the time of issuance of the ascending instruction, comprising:
   causing the storage unit to store the height of the table top at a time of issuance of the ascending instruction; and
   descending the table top to the stored height when the descending instruction is issued.

\* \* \* \* \*